(12) United States Patent
Sakuragi

(10) Patent No.: US 8,074,797 B2
(45) Date of Patent: Dec. 13, 2011

(54) STORAGE RECEPTACLE FOR USED SUTURE NEEDLES

(76) Inventor: Hitoshi Sakuragi, Kyoto (JP)

( * ) Notice: Subject to any disclaimer, the term of this patent is extended or adjusted under 35 U.S.C. 154(b) by 0 days.

(21) Appl. No.: 12/686,373

(22) Filed: Jan. 12, 2010

(65) Prior Publication Data

US 2011/0168592 A1 Jul. 14, 2011

(51) Int. Cl.
*B65D 83/10* (2006.01)

(52) U.S. Cl. ........ 206/366; 206/365; 206/380; 206/460; 66/5

(58) Field of Classification Search .......... 206/366, 206/365, 364, 380, 381, 460, 63.5, 63.3, 206/495, 813, 484, 339, 820; 66/5, 6, 17
See application file for complete search history.

(56) References Cited

U.S. PATENT DOCUMENTS

| | | | | |
|---|---|---|---|---|
| 2,897,962 A | * | 8/1959 | Zackheim | 206/369 |
| 3,857,484 A | * | 12/1974 | Thyen | 206/227 |
| 4,151,913 A | * | 5/1979 | Freitag | 206/370 |
| 4,182,448 A | * | 1/1980 | Huck et al. | 206/380 |
| 4,254,862 A | * | 3/1981 | Barratt | 206/63.3 |
| 4,418,821 A | * | 12/1983 | Sandel | 206/370 |
| 4,436,205 A | * | 3/1984 | Horii | 206/530 |
| 4,886,165 A | * | 12/1989 | Annett | 206/370 |
| 5,181,609 A | * | 1/1993 | Spielmann et al. | 206/370 |
| 6,659,270 B2 | * | 12/2003 | Williamson et al. | 206/63.3 |
| 6,739,450 B2 | * | 5/2004 | Roshdy et al. | 206/63.3 |
| 2002/0088728 A1 | * | 7/2002 | Sugama | 206/370 |

* cited by examiner

*Primary Examiner* — Mickey Yu
*Assistant Examiner* — Rafael Ortiz
(74) *Attorney, Agent, or Firm* — Rutan & Tucker, LLP

(57) ABSTRACT

Needle storage receptacle for safely storing and disposing of used suture needles in the operating room. The receptacle is lent a structure having a plurality of linked needle-storing units and having film-anchoring portions at both right-and-left ends, with each needle-storing unit being provided with a mounting pad for adhering a used suture needle, a lid part for covering the mounting pad, and a grip tab in order that the lid part may be grasped when the needle storing unit is to be open/closed, with the mounting pads being provided with adhesive surfaces on the front and rear sides, the lid parts having an adhesive surface on the front side, and on the rear side being printed with marks in such a way when the lid parts are overlaid onto and stuck together with the mounting pads numerals may be recognized through the front side.

20 Claims, 3 Drawing Sheets

STORAGE RECEPTACLE FOR USED SUTURE NEEDLES

BACKGROUND OF THE INVENTION

1. Technical Field

The present invention relates to a needle-storage receptacle with which needles used in suturing in the operating room are encased in adhesive tape to allow the needles to be disposed of easily and safely, and, having encased the needles, on which numerals appear on the surface, facilitating the handling of a number of used needles.

2. Description of the Related Art

Consumable implements employed in surgery mandate strict administration in terms of the correspondence between the number brought into the operating area and the number following surgery. In an operation, if correspondence between the number brought into the operating area and the number following surgery cannot be obtained, giving rise to a suspicion of loss, the possibility that a needle(s) has been left in the patient will be suspected, which hangs up final suturing until the needle(s) is discovered, incurring delays in the operating time. This proves to be a significant burden on the patient and on the physicians and nurses who perform the surgery.

Meanwhile, suture needles employed in surgery are prepared in accordance with an operation and handled after suture by being placed on a tray, separated from the unused needles, wherein a problem has been that during the surgery, medical accidents in which physicians and nurses come into contact with and are pricked by the used needles occur.

Therein, the inventors devised the present needle receptacle so as not only to ease the handling and disposal of a number of suture needles that have been used in surgery, helping contribute to alleviating the labor of physicians and nurses, but also to prevent in the operating area medical accidents with physicians and nurses due to used needles.

BRIEF SUMMARY OF THE INVENTION

An object of the present invention is to make available a needle storage receptacle that serves to render safe and simple the handling and disposal of a number of suture needles that have been used in surgery, and that serves to prevent medical accidents with physicians and nurses in which they come into contact with and are pricked by used needles.

The invention as given in a first aspect is a needle storage receptacle for safely storing and disposing of used suture needles in the operating room, and is characterized in that: the needle storage receptacle has a plurality of needle-storing units and film-anchoring portions; each needle-storing unit is furnished with a mounting pad for adhering a used suture needle, a lid part for covering the mounting pad, and a grip tab in order that the lid part may be grasped when the needle storing unit is to be open/closed; the mounting pads and the lid parts are made from sheeting, between the mounting pads and the lid parts is a fold line or score, and the mounting pads have adhesive surfaces on the front side and the rear side; the lid parts have an adhesive surface on the front side, and on the rear side are printed with numerals in such a way as to enable their recognition as numerals when the lid parts are overlaid onto and stuck together with the mounting pads; and the film-anchoring portions are structures provided on both of right-and-left ends of the needle storage receptacle.

The invention as given in a second aspect is a needle storage receptacle for safely storing and disposing of used suture needles in the operating room, and is characterized in that: the needle storage receptacle has a plurality of needle-storing units and film-anchoring portions; each needle-storing unit is furnished with a mounting pad for adhering a used suture needle, a lid part for covering the mounting pad, and a grip tab whereby the lid part is grasped when the needle storing unit is open/closed; the mounting pads and the lid parts are made from sheeting, between the mounting pads and the lid parts is a fold line or score, and the mounting pads have adhesive surfaces on the front side and the rear side; the lid parts have an adhesive surface on the front side, and on the rear side are printed with numerals in such a way as to enable their recognition as numerals when the lid parts are overlaid onto and stuck together with the mounting pads; adjoining needle-storing units each have a gap between them; and the film-anchoring portions are structures provided on either right-and-left ends of the needle storage receptacle.

The invention as given in a third aspect is the needle storage receptacle as given in the first or second aspects, characterized in that the rear side of the lid parts are not printed with numerals.

The invention as given in a fourth aspect is the needle storage receptacle as given in any of the first through third aspects, characterized in that the grip tabs of the needle-storing units have an elevated structure providing a slight angle from the plane containing the mounting pads and the lid parts, so as to ease gripping and opening/closing of the needle storing units.

The invention as given in a fifth aspect is the needle storage receptacle as given in any of the first through fourth aspects, characterized in that the sheeting employed in each needle-storing unit may be semitransparent, translucent white, or opaque.

The invention as given in a sixth aspect is the needle storage receptacle as given in any of the first through fifth aspects, characterized in that rather than having a plurality of linked needle-storing units, it has a singular unit.

Utilizing a needle storage receptacle involving the present invention readily can: realize eased handling of a number of suture needles that have been used in surgery; realize alleviation of the burden on patients due to prolongation in the length of an operation, associated with the intricacies of handling a number of needles; and realize prevention of medical accidents with physicians and nurses, in which they come into contact with and are pricked by used needles in the operating area.

DETAILED DESCRIPTION OF THE INVENTION

Below, with reference to the drawings, an explanation of best modes for embodying the present invention will be made.

Embodying Mode 1

Embodying Mode 1 is a needle storage receptacle in which a predetermined number of needle-storing units composed of a mounting pad that adheres a used suture needle that has been used in surgery, a lid part that is overlaid onto the mounting pad to cause the needle to cling to the pad, and a grip tab that is used in opening/closing the lid part are linked.

Figure 1:
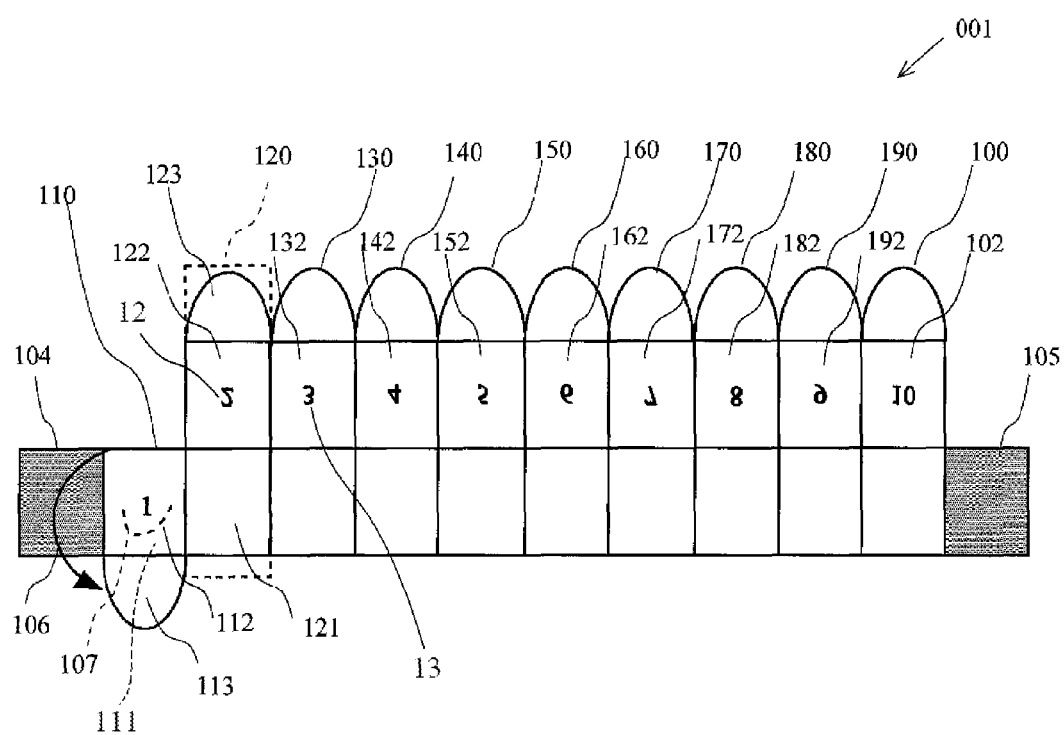
FIG. 1 is a plan view depicting a general outline of the configuration of a needle storage receptacle, composed of a plurality of needle-storing units, involving Embodying Mode 1.

Reference is made to FIG. 1, a plan view depicting a general outline of the configuration of a needle storage receptacle, composed of a plurality of the needle-storing units, involving Embodying Mode 1.

The needle-storing units in FIG. 1 are made from sheeting, wherein, in order from the left, ten units—110 (in FIG. 1, a state in which the grip tab and the lid part have been folded over onto the mounting pad is illustrated), 120, 130, 140, 150, 160, 170, 180, 190 and 100—are linked, and further, film-anchoring portions 104 and 105 are provided on both the left and right ends, constituting a needle storage receptacle 001. It will be appreciated that the number of needle-storing units in the connected series is not limited to ten.

The needle-storing unit 120 is furnished with a mounting pad 121 that adheres a used suture needle, a lid part 122 that is overlaid onto the mounting pad, and a grip tab 123 in order that the lid part may be grasped when the needle storing unit is to be open/closed, with the other needle-storing units having the same structure. As illustrated at needle-storing unit 110, the grip tab 113 is grasped to fold the lid part 112 over as indicated by the arrow 106 and lay it onto the mounting pad 111, encasing a needle inside, whereby the needle is securely captured adhesively and stored between the adhesive surfaces of the lid part 112 and the mounting pad 111.

On the lid part of each needle-storing unit, in order from the left, 112 (in FIG. 1, it is laid onto the mounting pad 121), 122, 132, 142, 152, 162, 172, 182, 192 and 102, the numerals "1," "2," "3," "4," "5," "6," "7," "8," "9" and "10" are printed as display numbers, on the rear side of the lid part of each needle-storing unit, so that when each grip tab is grasped to fold the lid part over and stick it onto the mounting pad and seal a needle inside, a numeral can be read from the front side. Reference mark 12 shows where the display numeral "2" has been printed, while reference mark 13 shows where the display numeral "3" has been printed. It will be appreciated that with numerals printed on the lid rear side in implementations in which the constituent film is transparent, through the front side recognition of numerals appearing vertically symmetrical would be possible.

In addition, the film-anchoring portions 104 and 105 provided on both the right and left ends are utilized in instances in which the adhesive force provided on the underside portion of the mounting pad of each needle-storing unit has weakened, such that the anchoring of the needle-storing units onto the sheet over the scrub nurse's instrument stand is insufficient, or in instances in which the adhesive surface on the rear side of the mounting pad has peeled off, wherein the anchoring portions 104 and 105 are grasped with forceps to reinforce the anchoring of the needle storage receptacle. Also, the sheeting employed in the film-anchoring portions 104 and 105 may be a colored film, distinct from the color of the sheeting employed in the needle-storing units.

Figure 2:
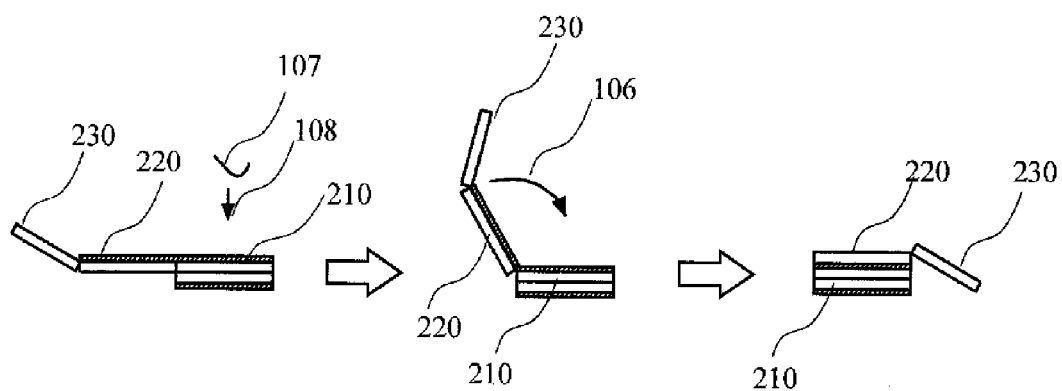
FIG. 2 is an explanatory diagram for explaining a method of sealing a used needle into a needle-storing unit.

Reference is made to FIG. 2, an explanatory diagram for describing how a used needle is sealed inside a needle-storing unit.

A needle 107 that is to be discarded is, as indicated by the arrow 108 in the figure, placed onto the front-side portion of the mounting pad 210. Next the grip tab 230 is grasped to lift the lid part 220 and, as indicated by the arrow 106, the lid part 220 is folded over and laid onto the mounting pad 210. By the film of the lid part and of the mounting pad adhering and closing shut, the needle 107 is completely sealed inside.

Figure 3:
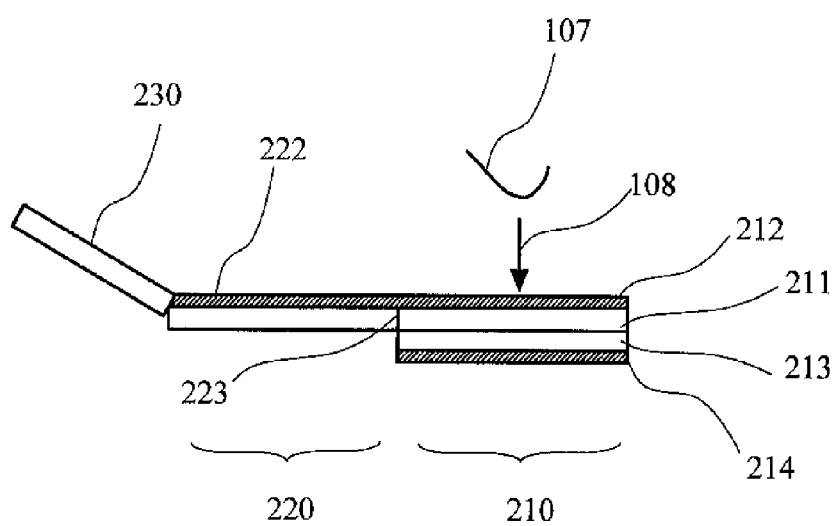
FIG. 3 is an explanatory side-view diagram for explaining a needle-storing unit where a used needle clings and is stored.

Reference is made to FIG. 3, a side-view diagram of the needle-storing unit in FIG. 2. The needle-storing unit has the lid part 220, the mounting pad 210, and the grip tab 230, with an adhesive surface 222 being provided on the front-side portion of the lid part 220, and with a fold line or score 223 being provided in between the mounting pad 210 and the lid part 220, facilitating folding of the unit.

The mounting pad 210 is provided on its front-side portion 211 with an adhesive surface 212 for adhering a used needle 107 and the lid part 220, and is provided on its underside portion 213 with an adhesive surface 214 so that the needle-storing unit may be anchored for example to the sheet covering the instrument tray.

Embodying Mode 2

Figure 4:
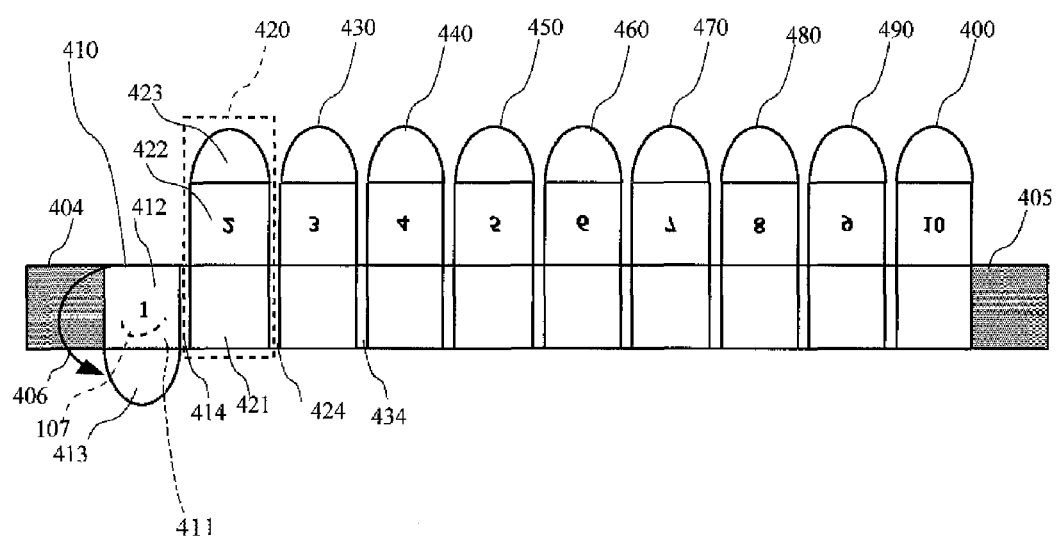
FIG. 4 is a plan view depicting a general outline of the configuration of a needle storage receptacle, composed of a plurality of needle-storing units, involving Embodying Mode 2.

Reference is made to FIG. 4, a plan view depicting a general outline of the configuration of a needle storage receptacle, composed of a plurality of needle-storing units, involving Embodying Mode 2.

The needle storage receptacle involving Embodying Mode 2, different from the needle storage receptacle of Embodying Mode 1, possesses a structure in which needle-storing units are linked, with each flanking a gap between it and the needle-storing unit that it adjoins. Ensuring the stability of the needle storage receptacle overall is therefore easier by comparison to the situation with the needle storage receptacle of Embodying Mode 1. In particular, in implementations in which the adhesive used on the adhesive surfaces is soft, even if the needle storage receptacle is subjected to external forces from various directions when being kept stored or during transport, the gaps opening between any two needle-storing units help prevent risk of any two neighboring needle-storing units becoming stuck together.

The needle storage receptacle involving Embodying Mode 2 is composed of a plurality of needle-storing units and the needle-storing units are made from sheeting, and in between adjoining needle-storing units the respective gaps are provided, forming a structure in which the needle-storing units are linked. In order from the left, ten units—410 (in FIG. 4, a state in which the grip tab and the lid part have been folded over onto the mounting pad is illustrated), 420, 430, 440, 450, 460, 470, 480, 490 and 400—are linked, respectively flanking a gap, and further, film-anchoring portions 404 and 405 are provided on both the left and right ends, constituting a needle storage receptacle. It will be appreciated that the number of needle-storing units in the connected series is not limited to ten.

The needle-storing unit 420 is structured having a gap 414 between it and the needle-storing unit 410 on its left, and having a gap 424 between it and the needle-storing unit 430 on its right, and the other needle-storing units are structured in the same way, having respective gaps.

The needle-storing unit 420 is composed of a mounting pad 421 that adheres a used suture needle, a lid part 422 that covers the mounting pad, and a grip tab 423 in order that the lid part may be grasped when the needle storing unit is to be open/closed, with the other needle-storing units possessing the same structure as does the unit 420. The use method, in which, as illustrated at needle-storing unit 410, the lid part 412 is folded over and laid onto the mounting pad 411, encasing a used needle inside, is the same as with the needle storage receptacle of Embodying Mode 1.

Also similar to the needle storage receptacle of Embodying Mode 1 is that on the lid part of each needle-storing unit, in order from the left, 412 (in FIG. 4, it is laid onto the mounting pad 411), 422, 432, 442, 452, 462, 472, 482, 492 and 402 (in FIG. 4, after 422, 432~402 have been omitted because they are the same as in FIG. 1), the numerals "1," "2," "3," "4," "5," "6," "7," "8," "9" and "10" are printed as display numbers, on the rear side of the lid part of each needle-storing unit, so that when the lid part is folded over and stuck onto the mounting pad to seal a needle inside, a numeral can be read from the front side.

Further, inasmuch as the film-anchoring portions 404 and 405 on both the left and right ends serve in a similar capacity to those of the needle storage receptacle of Embodying Mode 1, an explanation of their roles is omitted.

It should be understood that there are no particularities as to the material, etc. of the sheeting employed in the needle storage receptacles of Embodying Modes 1 and 2; since the sheeting may be that which is publicly known, an explanation thereof is omitted. For the film-anchoring portions (104 and 105 in FIG. 1; 404 and 405 in FIG. 4) provided on both the left-and-right ends of the needle storage receptacle and utilized in reinforcing, a colored film may be employed; while for the sheeting employed in the needle-storing units that, by the lid parts being folded over and stuck onto the adhesive surfaces, assume the role of adhesively capturing and storing used needles, it may be a semitransparent, a translucent white, or an opaque film.

What is claimed is:

1. A needle storage receptacle for safely storing and disposing of used suture needles in the operating room, the needle storage receptacle comprising:
   one or more needle-storing units, each needle-storing unit being open/closable along a fold line or score and furnished with
      a mounting pad made from sheeting and having adhesive surfaces on front and rear sides thereof,
      a lid part demarcated from said mounting pad by the fold line or score, said lid part for covering said mounting pad, said lid part being made from sheeting and having an adhesive surface on a front side thereof, wherein said lid part adhesive surface adheres to one of said mounting pad adhesive surfaces to securely capture and store a used suture needle, and
      a grip tab in order that said lid part may be grasped when the needle storing unit is to be open/closed; and
   film-anchoring portions, said film-anchoring portions being structures different from the needle-storing units and extending outward from said units, said film-anchoring portions provided on both of right-and-left ends of the needle storage receptacle.

2. A needle storage receptacle as set forth in claim 1, comprising a plurality of the needle-storing units adjoining each other.

3. A needle storage receptacle as set forth in claim 2, wherein adjoining needle-storing units each have a gap between them.

4. A needle storage receptacle as set forth in claim 1, wherein a rear side of said lid part is printed with a numeral in such a way as to enable its recognition as a numeral when said lid part is overlaid onto and stuck together with said mounting pad.

5. A needle storage receptacle as set forth in claim 3, wherein a rear side of said lid part is printed with a numeral in such a way as to enable its recognition as a numeral when said lid part is overlaid onto and stuck together with said mounting pad.

6. A needle storage receptacle as set forth in claim 1, wherein each grip tab of the one or more needle-storing units has an elevated structure providing a slight angle from a plane containing said mounting pad and said lid part, so as to ease gripping and opening/closing of the needle storing units.

7. A needle storage receptacle as set forth in claim 3, wherein each grip tab of the one or more needle-storing units has an elevated structure providing a slight angle from a plane containing said mounting pad and said lid part, so as to ease gripping and opening/closing of the needle storing units.

8. A needle storage receptacle as set forth in claim 4, wherein each grip tab of the one or more needle-storing units has an elevated structure providing a slight angle from a plane containing said mounting pad and said lid part, so as to ease gripping and opening/closing of the one or more needle storing units.

9. A needle storage receptacle as set forth in claim 5, wherein each grip tab of the one or more needle-storing units has an elevated structure providing a slight angle from a plane containing said mounting pad and said lid part, so as to ease gripping and opening/closing of the one or more needle storing units.

10. A needle storage receptacle as set forth in claim 1, wherein the sheeting employed in each needle-storing unit is semitransparent, translucent white, or opaque.

11. A needle storage receptacle as set forth in claim 3, wherein the sheeting employed in each needle-storing unit is semitransparent, translucent white, or opaque.

12. A needle storage receptacle as set forth in claim 4, wherein the sheeting employed in each needle-storing unit is semitransparent, translucent white, or opaque.

13. A needle storage receptacle as set forth in claim 5, wherein the sheeting employed in each needle-storing unit is semitransparent, translucent white, or opaque.

14. A needle storage receptacle as set forth in claim 6, wherein the sheeting employed in each needle-storing unit is semitransparent, translucent white, or opaque.

15. A needle storage receptacle as set forth in claim 7, wherein the sheeting employed in each needle-storing unit is semitransparent, translucent white, or opaque.

16. A needle storage receptacle as set forth in claim 8, wherein the sheeting employed in each needle-storing unit is semitransparent, translucent white, or opaque.

17. A needle storage receptacle as set forth in claim 9, wherein the sheeting employed in each needle-storing unit is semitransparent, translucent, white, or opaque.

18. A needle storage receptacle comprising: a plurality of needle-storing units, each needle-storing unit opening and closing along a fold line or score and including: a mounting pad having a front side adhesive surface and a rear side adhesive surface;
   a lid part demarcated from said mounting pad by the fold line or score and covering the mounting pad, the lid part having an adhesive surface on a front side thereof that is adjacent to, and adheres to, the mounting pad front side adhesive surface to securely capture and store a used suture needle; and a grip tab to open and close the needle storing unit; and first and second film-anchoring portions distinct from the needle storing units and extends outward from said units, the film-anchoring portions positioned respectively at opposing first and second ends of the needle storage receptacle.

19. A needle storage receptacle as set forth in claim 18, wherein a gap separates adjoining needle-storing units.

20. A needle storage receptacle as set forth in claim 18, wherein a rear side of each lid part includes a different printed numeral to enable its recognition as a numeral when the lid part is overlaid onto, and adhered to, the mounting pad.

* * * * *